(12) United States Patent
Zacche' et al.

(10) Patent No.: US 7,603,946 B2
(45) Date of Patent: Oct. 20, 2009

(54) PRESSURIZATION DEVICE

(75) Inventors: Vanni Zacche', Parma (IT); Alessandro Gorbi, Parma (IT); Massimiliano Dal Cielo, Parma (IT); Phuchakr Pringpuangkeo, Parma (IT)

(73) Assignee: Sidel S.p.A., Parma (IT)

( * ) Notice: Subject to any disclaimer, the term of this patent is extended or adjusted under 35 U.S.C. 154(b) by 485 days.

(21) Appl. No.: 10/492,957

(22) PCT Filed: Oct. 23, 2001

(86) PCT No.: PCT/IT01/00538

§ 371 (c)(1),
(2), (4) Date: Nov. 22, 2004

(87) PCT Pub. No.: WO03/035120

PCT Pub. Date: May 1, 2003

(65) Prior Publication Data

US 2005/0072319 A1    Apr. 7, 2005

(51) Int. Cl.
*A61L 2/00*    (2006.01)
*A23L 3/015*   (2006.01)

(52) U.S. Cl. .......................... 99/452; 99/460; 99/467; 422/295; 422/292

(58) Field of Classification Search .............. 99/467, 99/485, 452, 453, 460, 461, 473; 422/295, 422/292, 296; 92/86, 169.1, 169.2
See application file for complete search history.

(56) References Cited

U.S. PATENT DOCUMENTS

| | | | | |
|---|---|---|---|---|
| 4,984,507 A * | 1/1991 | Suzuki et al. | ............. | 91/376 R |
| 5,470,547 A | 11/1995 | Lhenry | | |
| 5,579,682 A | 12/1996 | Bergman et al. | | |
| 5,622,678 A * | 4/1997 | Hiltawsky et al. | ........... | 422/295 |
| 5,948,356 A * | 9/1999 | Lhenry et al. | ................. | 422/39 |
| 6,899,175 B2 * | 5/2005 | Kostrov et al. | .............. | 166/249 |

FOREIGN PATENT DOCUMENTS

EP    1 048 608 A1    11/2000
FR    2 781 413 A1    1/2000

* cited by examiner

*Primary Examiner*—Reginald L Alexander
(74) *Attorney, Agent, or Firm*—Hogan & Hartson, LLP (57) ABSTRACT

The present invention relates to a pressurization device, in particular of the type used for high hydrostatic pressure. More particularly, the present invention relates to a pressurization device (1) comprising a casing (4) provided with a closure (3) and housing a pressurization chamber (15), the device (1) being provided with pressurization means for putting the pressurization chamber (15) under pressure, characterized in that the pressurization chamber (15) is sealed by means of a plurality of annular seals (19a, 19b, 19c) arranged in series on the lateral surface of the pressurization chamber (15) at predetermined relative distances (D1, D2) which are correlated with the coefficient of compressibility of the liquid filling the pressurization chamber (15).

19 Claims, 8 Drawing Sheets

PRESSURIZATION DEVICE

The present invention relates to a pressurization device, in particular of the type used for high hydrostatic pressure.

There are various methods of sterilizing/pasteurizing foods and their containers.

A first method provides for the sterilization of the foods or beverages by a heat treatment and for their packaging at high temperature in order to utilize their thermal energy as an agent for sterilizing the container. This method can be used with containers the physical/chemical characteristics of which do not change at the filling temperature, and is generally used with glass or aluminium containers (cans) or with recrystallized PET containers.

A second method provides for the sterilization of the foods by a heat treatment prior to packaging which is then carried out at ambient temperature, in an aseptic chamber, in a previously sterilized container. This system presupposes the sterilization of the container with chemical/physical agents and the maintenance of an aseptic environment during the packaging and sealing stage with the use of suitable sterile chambers (known as "white chambers") having a volume of a few cubic meters, which chambers are difficult to control in an industrial environment.

The spread, in recent years, of new dietary products and products to which vitamins and/or microelements important for supplementing the diet have been added has given rise to the need to provide alternative sterilization methods to those using heat so as to avoid irreversible processes which denature the product.

Amongst the various methods used—the use of pulsed electric fields, magnetic fields, microwaves etc.—the method based on the use of hyperbaric chambers, in which sterilization is achieved by the maintenance of high hydrostatic pressure, has recently gained particular importance. It is known that the application of high pressure induces morphological changes in the cells of micro-organisms, which may extend to rupture of the cell membrane and consequent death of the micro-organism.

The extent and early occurrence of the changes induced by the high pressure depend on various factors, amongst which are the intensity of the pressure, the time for which it is applied, and the type of compression/decompression cycle used.

The use of the hydrostatic-pressure sterilization method in the food industry is known. However, the method has the disadvantage of being discontinuous since it provides for the use of large hyperbaric chambers in which a batch of products to be sterilized is inserted. Moreover, it is characterized by long sterilization-cycle times which are due partly to the time required by the apparatus to reach the working pressure and to return to atmospheric pressure upon completion. The known method therefore clearly has little versatility and does not permit adequate productivity of the plant.

To prevent these problems, apparatus has been proposed for the sterilization of beverages at high pressure, for which continuous, linear or rotary apparatus is provided and comprises a plurality of high-pressure sterilization chambers, each of which can hold one bottle. This solution is covered by European patent application EP 1 048 608 published on 2 Nov. 2000.

Although this apparatus substantially solves the problems inherent in the apparatus and methods of the prior art, it has some disadvantages. In fact, the operation of the sterilization device as conceived in the above-mentioned patent application is complex, particularly with regard to the kinematic mechanism for the insertion of the bottles in the device and their removal therefrom.

A further disadvantage of known apparatus operating at pressures of a few thousand atmospheres is connected with the difficulty of ensuring effective and durable sealing of the pressurization chamber. In particular, the seals are subject to wear such as to require their replacement after a few weeks of continuous working, which requires the use of expensive special seals.

The problem underlying the present invention is therefore that of providing a pressurization device which overcomes the disadvantages set out above.

This problem has been solved by a pressurization device as defined in the appended claims.

Further characteristics and advantages of the pressurization device of the present invention will become clearer from the description of some preferred embodiments thereof, given below by way of non-limiting example, with reference to the appended drawings, in which.

With reference to the drawings, the pressurization device according to the invention, generally indicated 1, comprises, basically, a hollow body 2 and a cover 3 connected movably to the body 2.

Figure 1:
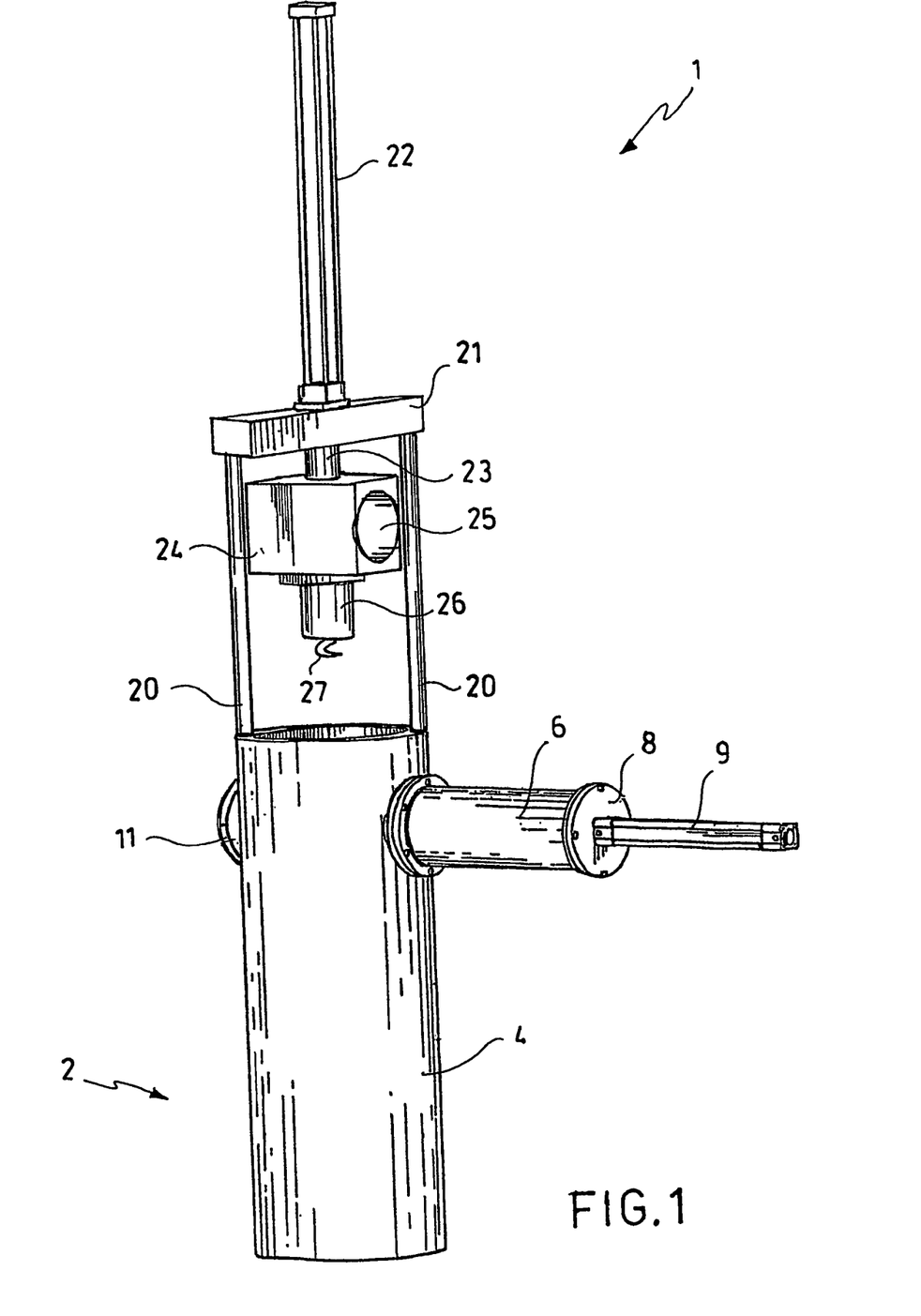
FIG. 1 is a perspective view of the pressurization device of the invention in the non-operative condition.
Figure 2:
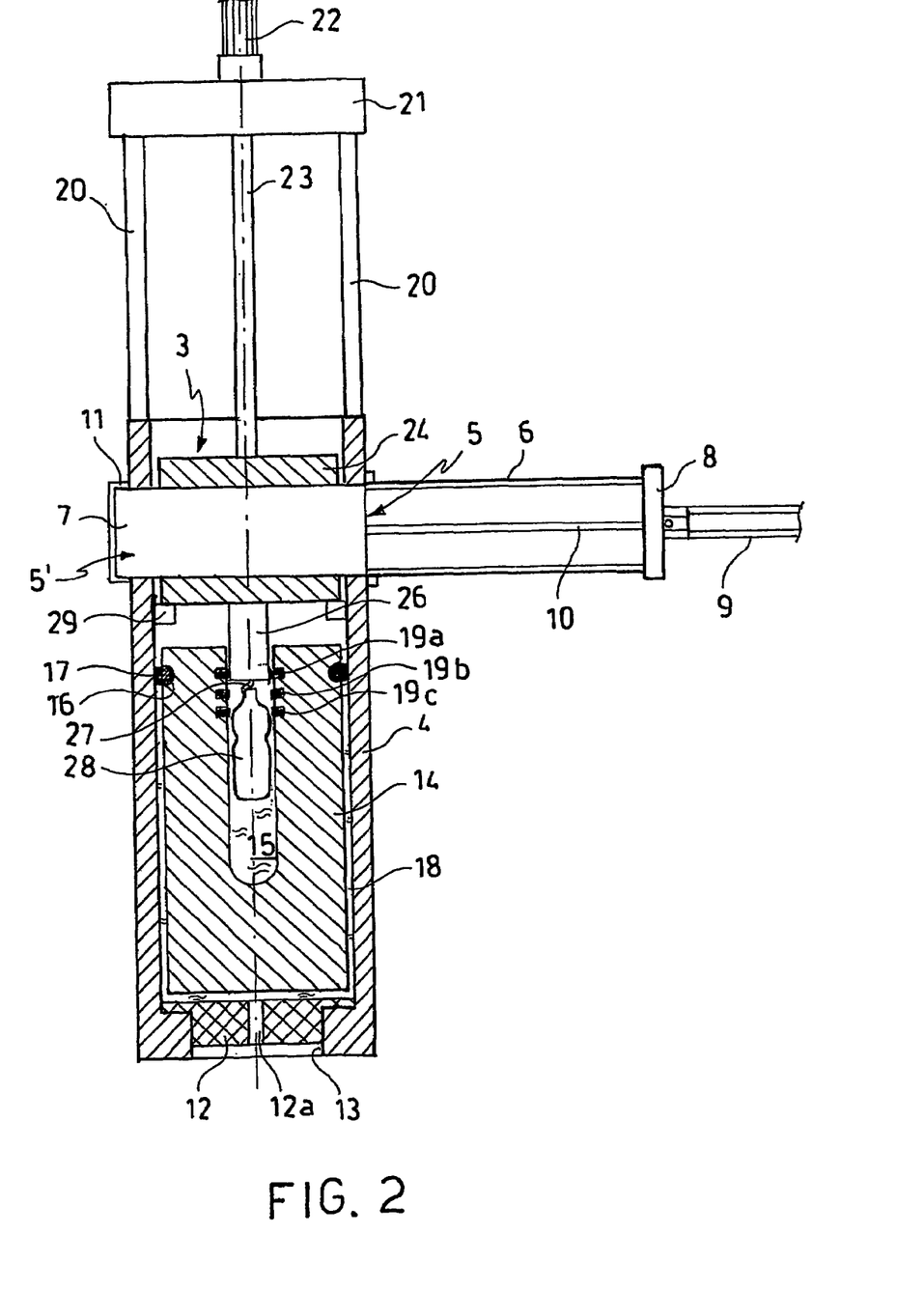
FIG. 2 is a side view showing the device of FIG. 1 in section.

As shown in FIGS. 1 and 2, the hollow body 2 comprises a substantially cylindrical casing 4 which is open at its two ends. Two aligned holes 5, 5' are formed in the cylindrical lateral surface of the casing 4, in the portion close to its upper end which is to receive the cover 3.

A cylindrical guide 6 for a pin 7 for securing the cover 3 is fixed to the first hole 5, as will be explained further in the following description. The end of the guide 6 which is inside the casing 4 is open, whereas its outer, opposite end is closed by a closure disk 8. An actuator 9, preferably a linear actuator, more preferably a brushless motor or an oleodynamic cylinder, is mounted externally on the disk 8. The disk 8 has a central hole through which the shaft 10 of the actuator 9 extends and, in turn, is fixed to the outer end of the pin 7.

Fixed to the second hole 5', on the other hand, is a sleeve 11 having its outer end closed and its inner end open.

The inside diameters of the guide 6 and of the sleeve 11 are substantially equal and correspond to the diameter of the pin 7 so as to allow the pin to slide inside them. Moreover, the guide 6 and the sleeve 11 lie on the same axis, which is substantially perpendicular to the principal axis of the casing 4.

The casing 4 is sealed at the bottom by a cylindrical closure element 12 with a T-shaped cross-section which has its larger base bearing on an annular shoulder 13 formed in the region of the lower end of the casing 4, and which projects inwardly. A duct 12a extends through the closure element 12 and is connected externally to a hydraulic system 40 which, in the embodiment described herein, constitutes the pressurization means 133 of the device.

A hollow pressurization cylinder 14, open at its upper end, is arranged in a floating condition inside the casing 4 so that a pressurization chamber 15 is defined within the cylinder 14.

An annular seal 17 is disposed in a corresponding seat 16 on the outer lateral surface of the pressurization cylinder 14, in the vicinity of its upper end. The outside diameter of the pressurization cylinder 14 is less than the inside diameter of the casing 4 so as to define a space 18 which is intended to be filled up to the level of the annular seal 17 with hydraulic oil or other substantially incompressible fluid.

Three annular seals 19a, 19b, 19c are arranged in series in suitable seats on the inner surface of the pressurization cylinder 14, in the vicinity of its open upper end. The relative distances D1, D2 between the first and second annular seals 19a, 19b and between the second and third annular seals 19b, 19c, respectively, are calibrated on the basis of the coefficient of compressibility of the fluid admitted to the pressurization chamber 15 so as to correspond to predetermined pressure increments, as will be described further below.

Two rods 20, extending upwards, are fixed to the upper edge of the casing 4. The upper ends of the rods 20 are fixed to a plate 21 to the upper surface of which an actuator 22, preferably a linear actuator, is fixed. The plate 21 has a hole in the region of the shaft 23 of the actuator 22 which thus protrudes below the plate 21.

The shaft 23 of the actuator 22 is fixed to the upper surface of the cover 3.

The body 24 of the cover 3 has a transverse through-hole 25 which has a diameter substantially corresponding to the diameter of the pin 7 and which is arranged in alignment with the pin when the cover is in the closed condition. The axial length of the hole 25 also corresponds substantially to the distance between the inner ends of the guide 6 and of the sleeve 11.

A substantially cylindrical plugging element 26 having a diameter slightly smaller than that of the pressure chamber 15 extends below the body 24 of the cover 3 so that a spacing is defined between the outer surface of the plugging element 26 and the walls of pressurization chamber 15. As will become clear from the following description, the plugging element 26, in association with the pressurization cylinder 14, forms pressure-multiplier means.

Means 27 for the engagement of the container 28 are fixed to the lower surface of the plugging element 26. The engagement means 27 are of known type and, in the embodiment shown in the drawing, take the form of a hook.

A flange 29 disposed on the inner surface of the casing 4, below the guide 6 and the sleeve 11, has the function of acting as stop means for the cover 3 when it is lowered into the casing 4 and when the plugging element 26 is disposed in the region of the first annular seal 19a.

The pressurization device of the present invention also comprises a pressure sensor 42 and, optionally, a temperature sensor 43, disposed inside the pressurization chamber 15, the sensors being connected to a control and operating unit 44, which provides for constant monitoring of the operative conditions of the system. It is thus possible to check that the sterilization process is executed correctly and consequently to discard defective containers or, in the event of a repeated processing error, to identify the breakdown of a device.

The pressurization device may also be provided with energy recovery means 129, the function of which is to recover some of the energy released by the system during the decompression stage which takes place upon completion of the pressurization cycle. In the embodiment shown in FIG. 2, in which pressurization takes place by means of a hydraulic system 40 provided with a pump 41 which injects the hydraulic oil into the space 18 at high pressure, energy recovery may take place by means of a turbine connected to a dynamo, or by means of potential energy accumulators 129 such as those described in International application No. PCT/IT01/00175 filed on 6 Apr. 2001, the description of which is incorporated herein by reference.

The pressurization device 1 according to the present invention may form part of food-packaging apparatus, for example, for performing the sterilization stage, but may also be used for processes of other types which require high-pressure treatment. Apparatus of this type may equally well be linear, rotary, or arranged along a path extending on one or more levels, and one or more pressurization devices according to the invention may be arranged in a movable or stationary manner therein. An example of apparatus in which the pressurization devices according to the present invention may be used is described in European patent EP 1 048 608 published on 2 Nov. 2000, the description of which is incorporated herein by reference. The apparatus will comprise means for continuously replenishing water (or other substantially incompressible fluid) inside the pressurization chamber so as to keep it constantly filled during all of the stages of the process.

The annular seals 17, 19a, 19b, 19c are generally made of a resilient polymer material.

The pressurization cylinder 14 is preferably made of a high-purity hardening and tempering steel, produced by re-melting in a controlled atmosphere.

The operation of the pressurization device of the present invention will now be described, again with reference to the drawings.

The step of the transfer of the container 28, which is a bottle in the drawing, from the conveyor system of the apparatus to the device 1 is not described since it is wholly conventional. The device is therefore shown in FIG. 2 with the bottle already secured to the engagement means 27 of the cover 3 and already inserted in the pressurization chamber 15. During the immediately preceding stage, the actuator 22 will have acted on the cover 3, causing it to slide downwards until the body 24 of the cover abutted the flange 29. In this position, the hole 25 is aligned with the pin 7, allowing the actuator 9 to act on the pin, thus causing it to advance through the hole 25 and to be housed in the sleeve 11. The pin 7 thus acts as a locking means for the cover 3 in order to contain the axial pressure generated during pressurization. The bottle is inserted in the pressurization chamber during the downward movement of the cover 3 and before its hole 25 is aligned with the pin 7. When the downward travel of the cover 3 stops, the plugging element 26 has reached the first annular seal 19a of the pressurization chamber 15, interacting therewith. The bottle will therefore be sealed inside the pressurization chamber 15 and completely immersed in water.

At this point, the pump of the hydraulic system will introduce the oil into the space 18 in the device at a predetermined pressure. The introduction of the oil into the space 18 under pressure causes the floating pressurization cylinder 14 to move upwards. Since the plugging element 26 is fixed, the lifting of the pressurization cylinder 14 causes compression of the fluid inside the pressurization chamber 15 and an increase in pressure, which, according to Pascal's principle, will be directly proportional to the ratio between the area of the base of the cylinder 14 and the area of the lower surface of the plugging element 26. If, for example, the hydraulic oil is injected into the space 18 at a pressure of 600 bar and if the ratio between the areas is 10, the pressure inside the pressurization chamber 15 will be multiplied by ten, thus reaching 6000 bar.

In greater detail, FIGS. 3a, 3b, 3c, 3d show, in sequence, the various pressurization stages, up to the reaching of the working pressure. In the following description, reference will always be made to the example considered above, which leads to the reaching of a working pressure of 6000 bar.

Figure 3A:
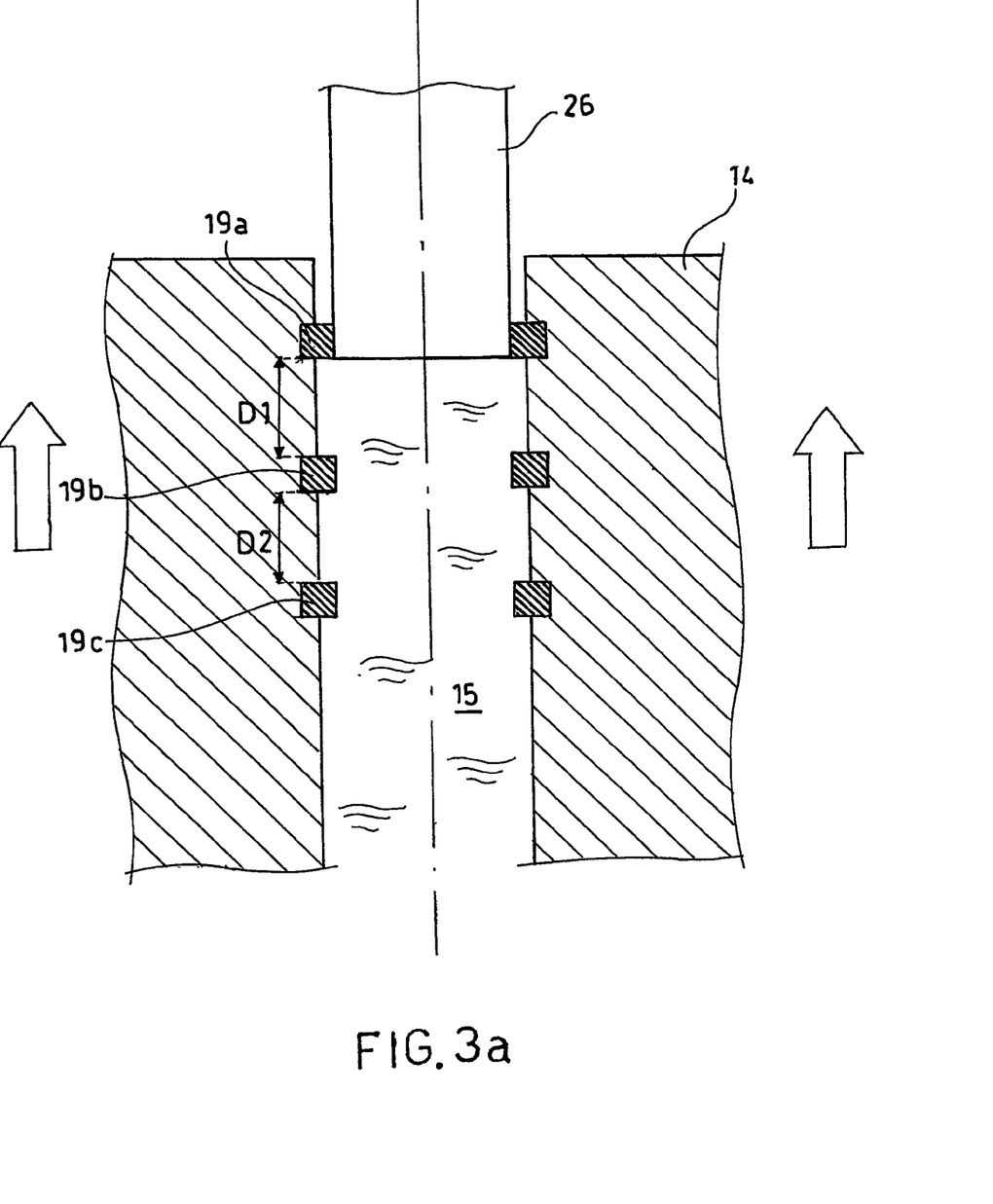
FIGS. 3a, 3b, 3c, 3d are views all showing, in section, the same detail of the device of FIG. 1, in accordance with an operative sequence.

FIG. 3a shows the initial stage in which the cover 3 has been lowered until it abuts the flange 29 and the plugging element 26 interacts with the first annular seal 19a. At this point, the hydraulic oil is injected into the space 18 so that the pressurization cylinder 14 is urged upwards in the direction of the arrow.

Figure 3B:
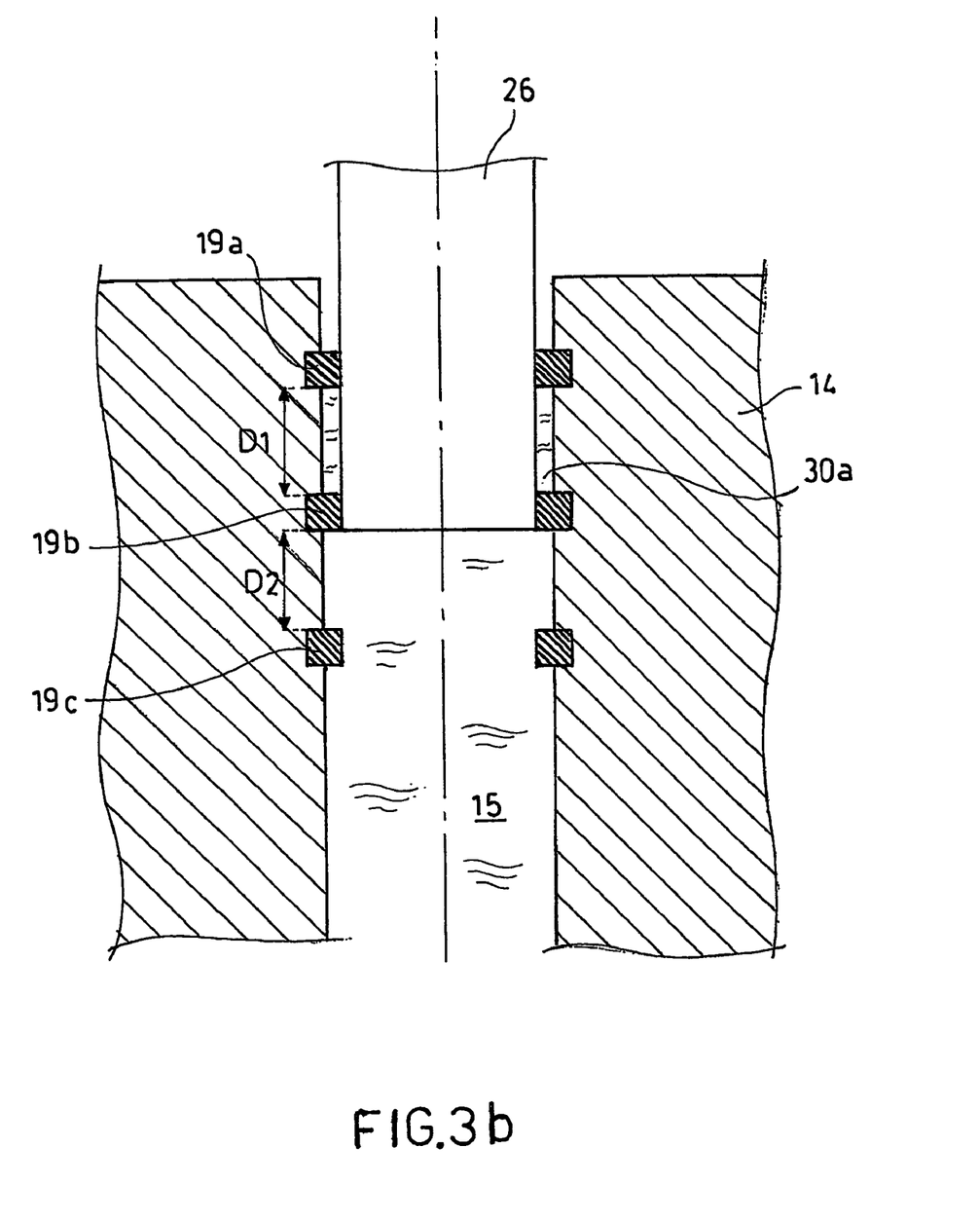

As shown in FIG. 3b, the plugging element 26 then starts to interact with the second annular seal 19b. The distance D1 between the two seals 19a, 19b corresponds to a compression of the water in the pressurization chamber 15 equal to 2000 bar. Similarly, the pressure in the space 30a defined between the first and second seals 19a, 19b, will be 2000 bar. The stress to which the first seal 19a will be subjected will therefore be 2000 bar, whilst the second seal 19b will be unloaded since the pressure is 2000 bar both in the pressurization chamber 15 and in the space 30a.

Figure 3C:
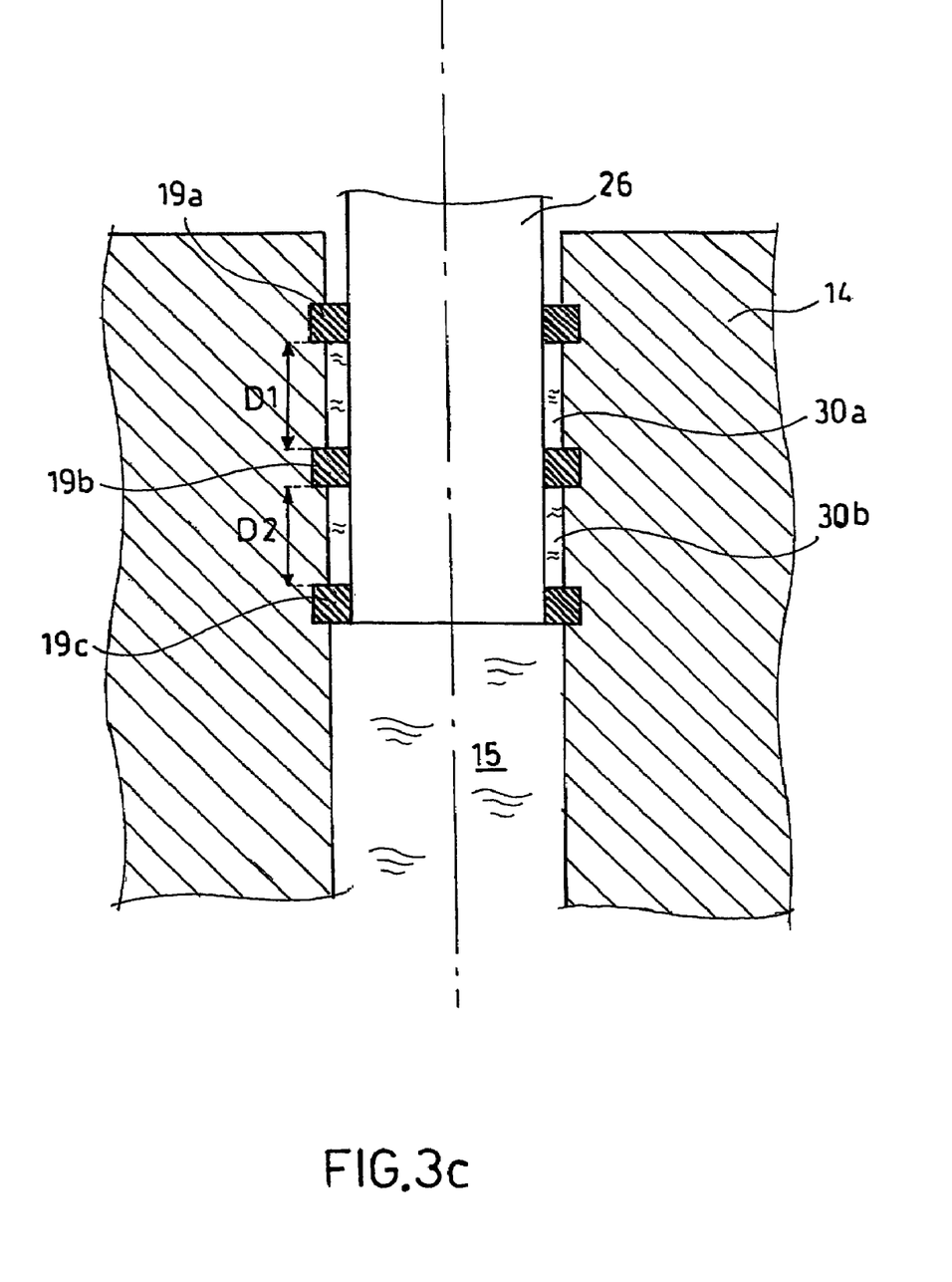

As shown in FIG. 3c, the next stage provides for the interaction of the plugging element 26 with the third seal 19c and the reaching of a pressure of 4000 bar inside the pressurization chamber 15, this pressure being dictated by the travel D2 of the pressurization cylinder 14. A pressure of 4000 bar will therefore also be reached in the space 30b defined between the second and third seals 19b, 19c. The second seal 19b will be subjected to a stress equal to the difference between the pressure in the space 30b (4000 bar) and the pressure in the space 30a, which will remain at 2000 bar, since the space 30a remains isolated by means of the two seals 19a and 19b. The stress on the second seal 19b is therefore 2000 bar again.

Figure 3D:
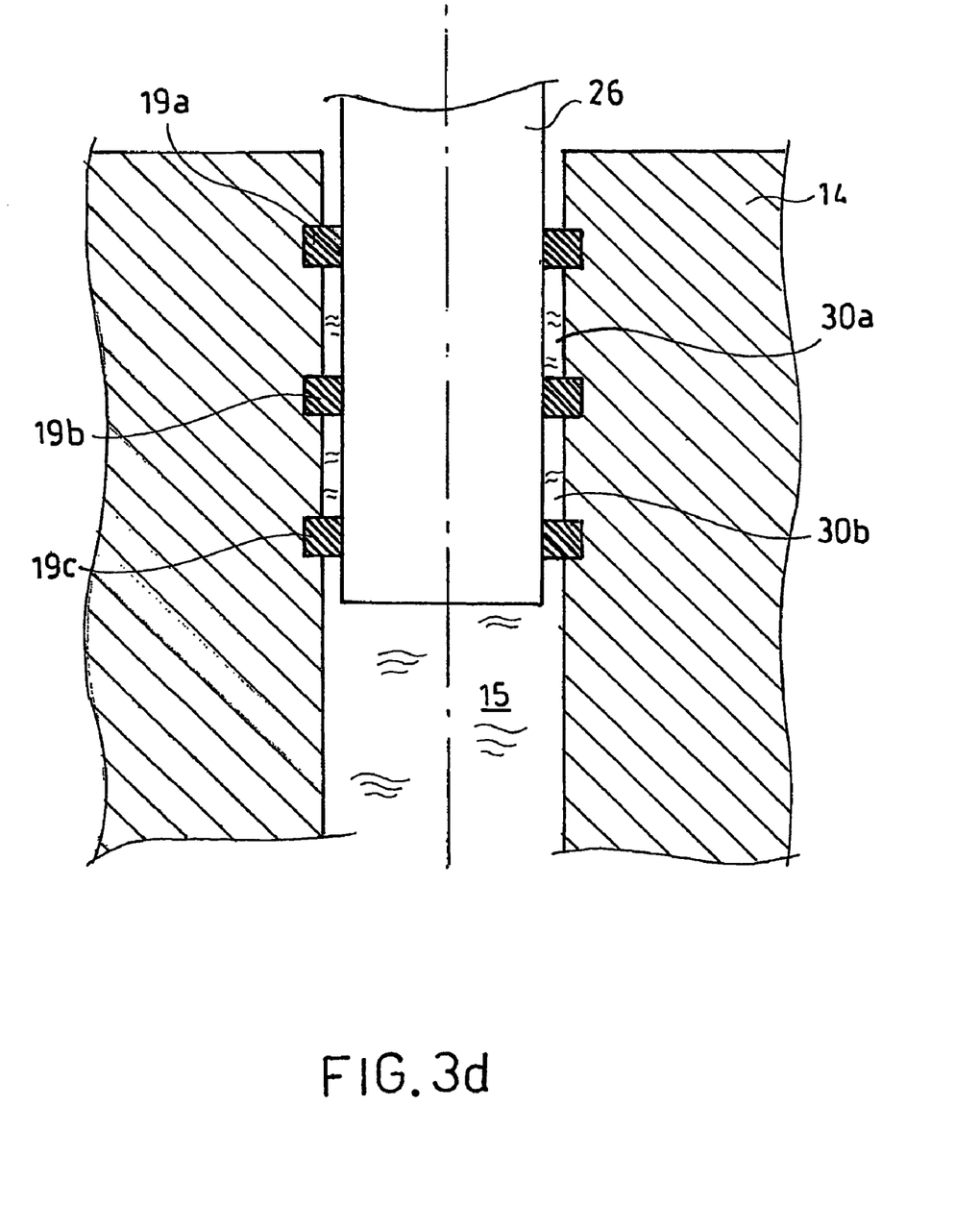

Finally, FIG. 3d shows the final pressurization stage in which the maximum pressure of 6000 bar, corresponding to a further upward travel of the pressurization cylinder 14, is reached. At this point, the third seal 19c is subjected to a stress equal to the difference between the pressure in the pressurization chamber 15 and in the space 30c (6000 bar) and the pressure in the space 30b, that is, 2000 bar again.

In general, it can be stated that, by means of the device of the invention, the seals of the pressurization chamber will be stressed by a pressure lower than the operative pressure inside the pressurization chamber. By virtue of the device of the invention, it is therefore possible even to reach very high pressures (6000 bar and more) inside the pressurization chamber 15, whilst the stress on the seals is reduced to relatively low levels such as the 2000 bar of the example, at which pressure commercially-available seals normally work. In fact, if it were necessary to reach pressures other than those given in the foregoing example,—which can be achieved by modifying the hydraulic-oil injection pressure and/or the ratio of areas between the base of the floating cylinder 14 and the lower surface of the plugging element 26—it would be possible to keep the pressure stress on the seals to a predetermined value by increasing or decreasing the number of seals 19a, 19b, 19c in series, and by setting the relative distances D1, D2 between one seal and the next in a manner such as to correspond to predefined pressure increments.

As stated above, the relative distances D1, D2 between the seals 19a, 19b, 19c are correlated with the coefficient of compressibility of the fluid filling the pressurization chamber 15 in the sense that, for a predetermined desired pressure differential between two seals, a greater coefficient of compressibility of the fluid will correspond to a greater relative distance between the seals. As is known, the coefficient of compressibility at a given temperature generally decreases as a function of an increase in the pressure to which the liquid is subject. This means that with equal pressure differentials (2000 bar in the example given above) the distance D1 between the first seal 19a and the second seal 19b (corresponding to a pressure increment from atmospheric pressure to 2000 bar) may be greater than the distance D2 between the second seal 19b and the third seal 19c (corresponding to a pressure increment from 2000 to 4000 bar).

The relative distances D1, D2 at which the annular seals 19a, 19b, 19c are arranged can be determined, after the volume of liquid present in the pressurization chamber 15 and the working temperature have been set, by means of suitable calibration curves of $\Delta V/\Delta P$, where $\Delta V$ is the change in volume which corresponds to a pressure increment $\Delta P$. When $\Delta V$ has been determined, the distances D1, D2 will be calculated, taking into account the geometrical dimensions of the pressurization chamber 15.

The decompression stage is achieved simply by suspending the action of the hydraulic system, which causes a rapid re-equilibration of the pressure to atmospheric pressure. The pressurization cylinder 14 returns and the oil initially admitted to the space 18 flows back, operating the energy-recovery means described above. The operation can be repeated by the implementation of a cycle of compressions/decompressions which is preferably of no more than 60 seconds' duration and which brings about the death of the micro-organisms present in the food or in the beverage within an extremely short time.

Upon completion of the pressurization stage and when the pressure in the pressurization chamber 15 has returned to atmospheric pressure, the actuator 9 withdraws the pin 7, releasing the cover 3. The cover is then raised by means of the actuator 22 which enables the container 28 to be removed and a new process to be started.

As stated above, the control and operating unit provides for the operation of the actuators and of the hydraulic system in accordance with the predetermined program, and for the monitoring of the entire process to detect malfunctions and breakdowns.

Figure 4:
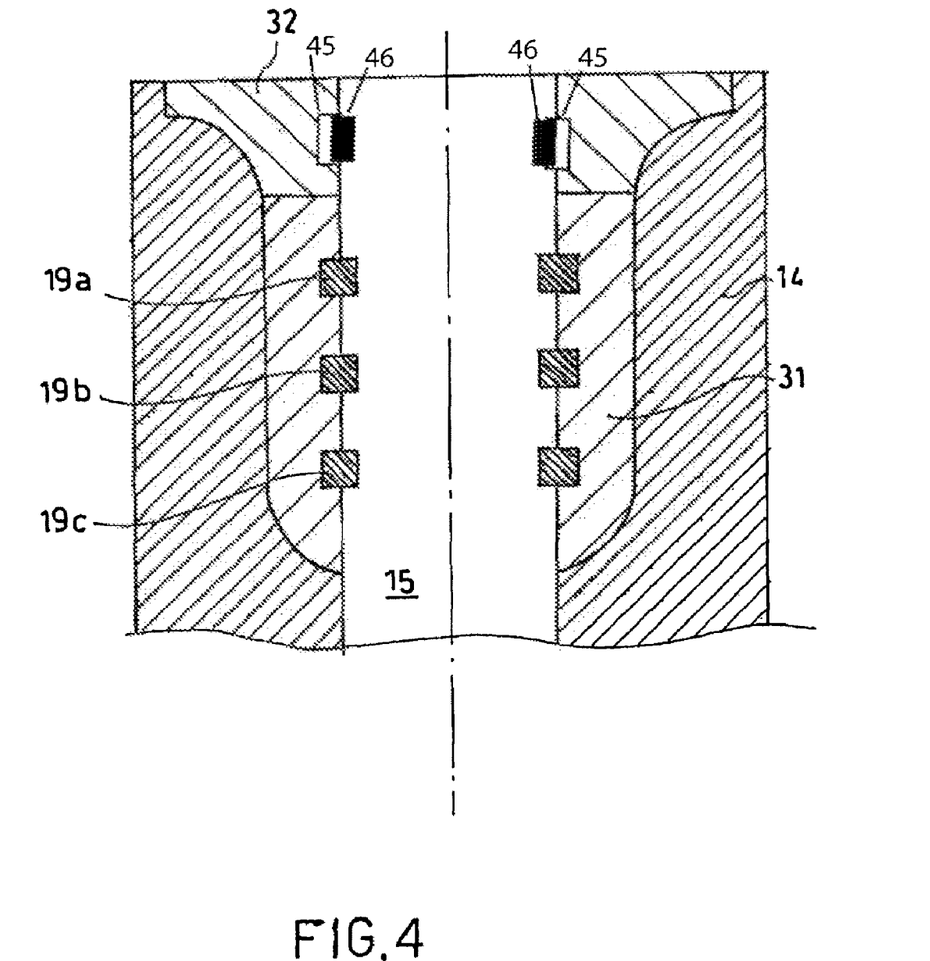
FIG. 4 shows, in section, a detail of a different embodiment of the pressurization device of the invention.

FIG. 4 shows a different embodiment of the invention in which the seals of the pressurization chamber 15 are rendered replaceable by virtue of the provision of a removable annular cartridge 31 carrying the annular seals 19a, 19b, 19c in suitable seats. A ring 32 disposed above the cartridge and secured to the body of the pressurization cylinder 14, for example, by screwing element 46 into element 45, will keep the cartridge 31 anchored to the cylinder. Different cartridges 31 may be provided, in which the number of seals and the relative distances D1, D2 between the annular seals 19a, 19b, 19c is pre-calibrated in dependence on the pressure to be reached and on the coefficient of compressibility of the liquid which is admitted to the pressurization chamber 15.

The advantages of the pressurization device according to the invention are clear from the foregoing description.

In the first place, the invention enables extremely high pressures to be reached inside the pressurization chamber 15 without overloading the seals the stresses on which are kept to a level which can easily be withstood, even by conventional seals.

The provision of a space 18 which surrounds the outer surface of the pressurization cylinder 14 and which is filled with hydraulic oil under pressure enables the radial thrusts generated inside the pressurization chamber 15 to be contained without the use of more expensive devices such as, for example, multi-layer jackets. Such jackets may, however be provided, particularly for very high pressures. The casing 4 does, however, have the function of containing the axial thrusts of the system and the minimal level of radial thrusts which are due to the admission of the hydraulic oil under pressure to the space 18, which thrusts, however, are normally limited to a few hundred bar.

The provision of pre-calibrated and interchangeable cartridges 31 carrying the annular seals 19a, 19b, 19c for sealing the pressurization chamber 15 enables the seals to be replaced quickly, either when they are worn or when a different pressurization liquid is to be used.

Figure 5:
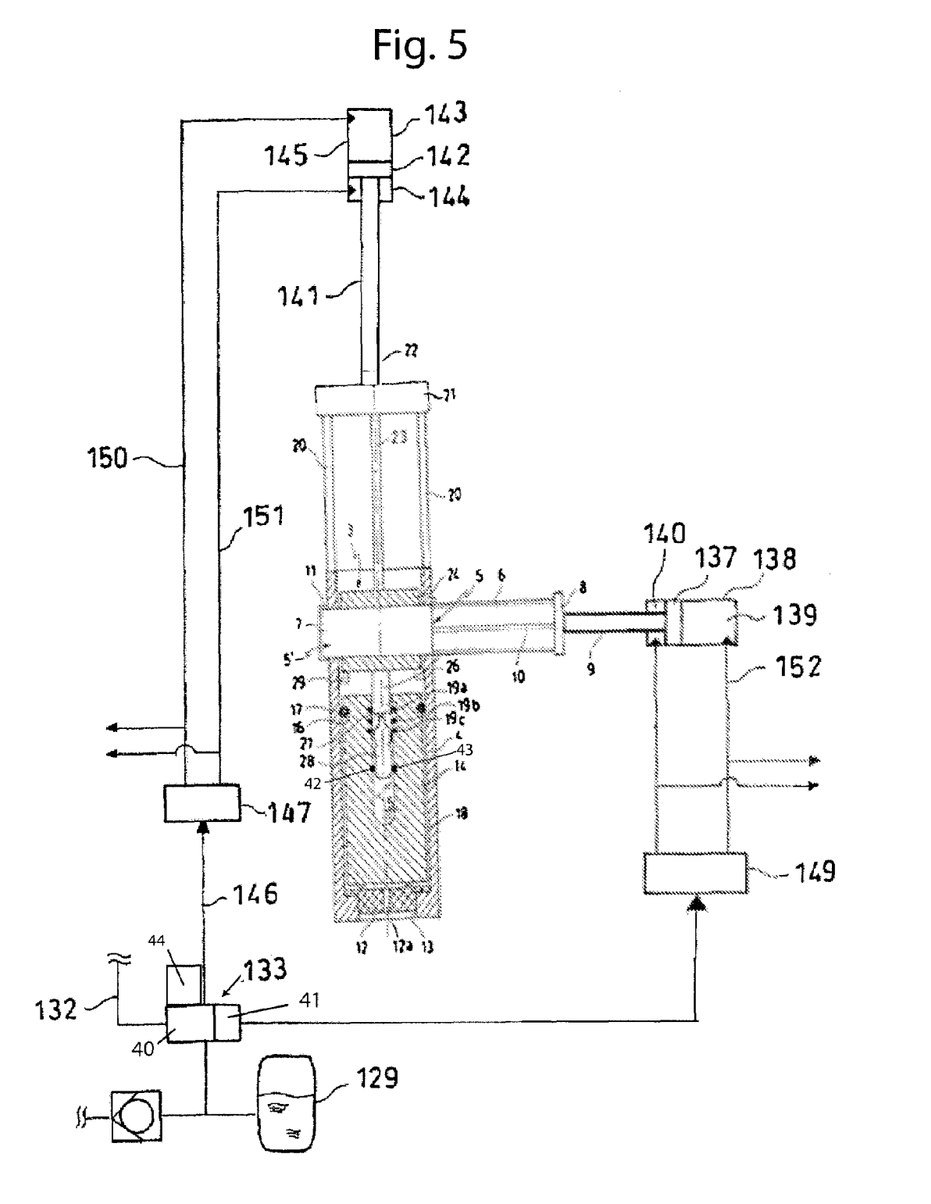
FIG. 5 is a partially-sectioned, schematic view of a detail of the pressurization system.

FIG. 5 illustrates an embodiment of the present invention comprising a thrust chamber 145, a pressurization means 133, and a piston 137. As shown in FIG. 5, the thrust chamber 145 comprises a housing 143, a piston 142, and a return chamber 144. Shaft 141 connects the pressure device 1 to return chamber 144. The closure control valve means 147 in turn has two outlets. The first outlet (also connected to secondary tube 132) is connected to a thrust tube 150 which brings hydraulic oil to the thrust chamber 145 of the closure—piston housing 143. The second outlet is connected to a return tube 151 which brings hydraulic oil to the return chamber 144 of the closure—piston housing 143. Both the thrust tubes 150, 152 and the return tubes 151, 153 are in flow communication with respective ducts which recirculate the oil to the space 18. Each of these ducts has valve means (not shown in the drawing) which open and close alternately. Duct 146 connects closure control valve means 147 to pressurization means 133. Duct 148 connects the pressurization means 133 to the control valve means 149. Thrust chamber 139 comprises a return chamber 140, a housing 138, and a piston 137.

The system for the closure/opening of the device is kinematically simple and hence not very liable to malfunction. It also permits rapid operation.

The loading of the container from above reduces the need to supply water (or other pressurization liquid) for refilling the pressurization chamber. In fact only the minimum quantity of water necessary to replace the water which is inevitably spilled during each operative cycle is required. Times are thus optimized and over-dimensioning of the recirculation pump is avoided.

The control and operating unit connected to the pressure sensor and, optionally, to the temperature sensor (an increase in internal temperature is inevitable during the compression stage), ensures good operation of the system, indicating breakdowns and malfunctions.

The energy-recovery means associated with the pressurization means help to optimize the process from the energy point of view.

The sterilization process which can be performed by means of the pressurization device according to the present invention is such that it can be used even for foods or beverages which would not withstand known processes without deterioration. A typical example of use is for beverages such as milk or beer.

Naturally, only specific embodiments of the pressurization device of the present invention have been described and a person skilled in the art will be able to apply thereto all modifications necessary for their adaptation to particular applications without, however, departing from the scope of protection of the present invention.

For example, the shape of the pressurization chamber may be adapted to the type of container to be processed, which may not even be a bottle, but, for example, a dish or the like.

The pressurization means and the pressure-multiplier means may be calibrated so as to impart the desired and predefined pressure to the fluid inside the pressurization chamber. The structure of the device may be modified so as better to withstand the pressures generated.

The above-described invention has a series of characteristics which could also be adapted to pressurization devices of the prior art. For example, the provision of the casing 4 for containing the axial loads and of the floating pressurization cylinder 14 are characteristics which can be adapted to all devices designed for a treatment in which a high-pressure stage is envisaged.

The invention claimed is:

1. Pressurization device for high hydrostatic pressure comprising a casing provided with a closure and housing a pressurization chamber, the device being provided with pressurization means for putting the pressurization chamber under pressure, characterized in that the pressurization chamber is sealed by means of a plurality of annular seals arranged in series on the lateral surface of the pressurization chamber at predetermined relative distances which are correlated with the coefficient of compressibility of the liquid filling the pressurization chamber.

2. Device according to claim 1 in which the closure is a cover comprising a plugging element provided with means for the engagement of the container to be processed, characterized in that the pressurization chamber and the plugging element are slidable relative to one another, the lateral surface of the plugging element being intended to engage each of the annular seals in sequence.

3. Device according to claim 1, in which the relative distances between the annular seals correspond to predefined pressure increments.

4. Device according to claim 1, in which the annular seals are stressed, in a working condition, by a pressure less than the operative pressure in the pressurization chamber.

5. Device according to claim 1, in which the device comprises locking means for the closure.

6. Device according to claim 1, in which the closure comprises a body having a through-hole and locking means, said locking means for the closure comprising a pin slidable in a guide, and a sleeve arranged in alignment with the pin in a diametrically opposed position on the casing, the through-hole and the pin being in alignment when the closure is in the closed condition.

7. Device according to claim 1, in which the internal surface of the casing comprises stop means for the closure.

8. Device according to claim 1, in which the internal surface of the casing comprises stop means for the closure and in which said stop means comprise a flange for abutting the body of the closure.

9. Device according to claim 1, in which the pressurization chamber is housed in the cavity of a floating pressurization cylinder disposed inside the casing.

10. Device according to claim 1, in which the pressurization chamber is housed in the cavity of a floating pressurization cylinder disposed inside the casing, wherein the outside diameter of the pressurization cylinder is less than the inside diameter of the casing so that a space to be filled with hydraulic oil or other substantially incompressible fluid is defined between the two surfaces.

11. Device according to claim 10 in which the upper portion of the outer surface of the pressurization cylinder comprises an annular seal for the fluid contained in the space.

12. Device according to claim 1, the device comprising pressure-multiplier means which can increase the pressure imparted by the pressurization means inside the pressurization chamber by a predefined factor, said predefined factor being substantially equal to the ratio between the area of the base of the pressurization cylinder and the area of the lower surface of the plugging element.

13. Device according to claim 1, in which the pressurization means are constituted by a hydraulic system provided with a pump, the hydraulic system being connected to the space in the pressurization device by means of a duct.

14. Device according to claim 1, the device comprising energy-recovery means connected to the pressurization means, the energy-recovery means preferably comprising a hydraulic potential-energy accumulator.

15. Device according to claim 1, the device comprising pressure sensors and, optionally, temperature sensors, connected to a control and operating unit.

16. Device according to claim 1, the device comprising pressure sensors and, optionally, temperature sensors, connected to a control and operating unit, in which the control and operating unit operates actuators and the pressurization means in accordance with a predetermined program and monitors the operative pressure, and optionally temperature, conditions of the process.

17. Device according to claim 1, comprising a removable annular cartridge on which the plurality of annular seals are arranged in suitable seats.

18. Device according to claim 17 in which the cartridge is anchored to the surface of the pressurization chamber by means of a ring disposed above the cartridge and in turn secured to the body of the pressurization cylinder, for example, by screwing.

19. Apparatus for performing a high-pressure treatment on articles to be processed, characterized in that it comprises one or more pressurization devices according to claim 1.

* * * * *